(12) United States Patent
Young

(10) Patent No.: US 11,801,045 B2  
(45) Date of Patent: Oct. 31, 2023

(54) SUTURE PASSING DEVICE AND METHODS OF USE THEREOF

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventor: Timothy Young, Natick, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE LIMITED, Singapore (SG)

( * ) Notice: Subject to any disclaimer, the term of this patent is extended or adjusted under 35 U.S.C. 154(b) by 563 days.

(21) Appl. No.: 17/252,781

(22) PCT Filed: Jul. 3, 2019

(86) PCT No.: PCT/US2019/040476  
§ 371 (c)(1),  
(2) Date: Dec. 16, 2020

(87) PCT Pub. No.: WO2020/010185  
PCT Pub. Date: Jan. 9, 2020

(65) Prior Publication Data  
US 2021/0251624 A1 Aug. 19, 2021

Related U.S. Application Data

(60) Provisional application No. 62/694,182, filed on Jul. 5, 2018.

(51) Int. Cl.  
*A61B 17/04* (2006.01)  
*A61B 17/00* (2006.01)

(52) U.S. Cl.  
CPC ............. *A61B 17/0469* (2013.01); *A61B 2017/00367* (2013.01)

(58) Field of Classification Search  
CPC ............ A61B 17/0469; A61B 17/0483; A61B 2017/00367  
See application file for complete search history.

(56) References Cited

U.S. PATENT DOCUMENTS 5,496,335 A * 3/1996 Thomason ......... A61B 17/0483  
606/205  
5,569,269 A * 10/1996 Hart .................. A61B 17/0483  
112/169

(Continued)

*Primary Examiner* — Ryan J. Severson  
(74) *Attorney, Agent, or Firm* — Burns & Levinson, LLP; Joseph M. Maraia; Marlo Schepper Grolnic (57) ABSTRACT

A suture passing device has a curved, slotted shaft with a piercing end and an integral suture grasper, allowing the surgeon to pierce through a first tissue portion with the device and extend a looped portion of monofilament loaded within the shaft into the repair site. The shaft is then rotated so that the monofilament is allowed to fall out of the shaft through the slot. The surgeon then pierces a second tissue portion with the device and extends the suture grasper to capture the looped portion of monofilament. The monofilament is retrieved through the second tissue portion and a suture is passed through the looped portion of the monofilament. Finally, the flexible member is used to pull the suture through the tissue and the suture can be tensioned to close the hip capsule.

20 Claims, 6 Drawing Sheets

(56) References Cited

U.S. PATENT DOCUMENTS

| | | | | |
|---|---|---|---|---|
| 5,618,290 A * | 4/1997 | Toy | A61B 17/0469 | 606/139 |
| 5,653,716 A * | 8/1997 | Malo | A61B 17/06109 | 606/139 |
| 5,817,111 A * | 10/1998 | Riza | A61B 17/06109 | 606/139 |
| 5,904,692 A * | 5/1999 | Steckel | A61B 17/0469 | 606/139 |
| 5,910,148 A * | 6/1999 | Reimels | A61B 17/06109 | 606/139 |
| 8,679,135 B2 * | 3/2014 | Stone | A61B 17/0469 | 606/144 |
| 9,364,214 B2 * | 6/2016 | Courage | A61B 17/0485 | |
| 10,098,631 B2 * | 10/2018 | Stewart | A61B 17/0483 | |
| 10,383,621 B2 * | 8/2019 | Gregoire | A61B 17/0469 | |
| 10,682,133 B2 * | 6/2020 | Torrie | A61B 17/0485 | |
| 11,583,269 B2 * | 2/2023 | Pisarnwongs | A61B 17/0469 | |
| 11,701,106 B2 * | 7/2023 | Bourland, III | A61B 17/0469 | 606/148 |
| 2004/0249393 A1 * | 12/2004 | Weisel | A61B 17/0469 | 606/144 |
| 2013/0218175 A1 * | 8/2013 | Auerbach | A61B 17/0483 | 606/148 |
| 2014/0012292 A1 * | 1/2014 | Stewart | A61B 17/0469 | 606/148 |
| 2014/0128889 A1 * | 5/2014 | Sullivan | A61B 17/0483 | 606/144 |
| 2014/0207188 A1 * | 7/2014 | Yearsley | A61B 17/0485 | 606/224 |
| 2015/0025550 A1 * | 1/2015 | Heneveld | A61B 17/0483 | 606/144 |
| 2015/0374359 A1 * | 12/2015 | Heneveld | A61B 17/0485 | 606/144 |
| 2016/0089135 A1 * | 3/2016 | Gregoire | A61B 17/0469 | 606/144 |
| 2017/0367693 A1 * | 12/2017 | Heneveld | A61B 17/0469 | |
| 2018/0116652 A1 * | 5/2018 | Torrie | A61B 17/06109 | |
| 2020/0345343 A1 * | 11/2020 | Pisarnwongs | A61B 17/06 | |
| 2020/0360013 A1 * | 11/2020 | Bourland, III | A61B 17/0469 | |
| 2021/0251624 A1 * | 8/2021 | Young | A61B 17/0485 | |

\* cited by examiner

SUTURE PASSING DEVICE AND METHODS OF USE THEREOF

CROSS-REFERENCE TO RELATED APPLICATIONS

This application is the U.S. national phase entry under 35 U.S.C. § 371 of International Application No. PCT/US19/40476, filed Jul. 3, 2019, entitled SUTURE PASSING DEVICE AND METHODS OF USE THEREOF, which in turn claims priority to and benefit of U.S. Provisional Application No. 62/694,182, filed Jul. 5, 2018, the contents of which are incorporated herein by reference in their entirety for all purposes.

FIELD

The present disclosure relates generally to surgical instruments and, in particular, to surgical instruments that can manipulate and pass suture through tissue.

BACKGROUND

Arthroscopic surgery typically involves the performance of surgical procedures through small openings in the body and under visualization using an endoscope. Access to a target tissue is normally provided through one or more portals formed directly in the patient's body or through one or more cannulas inserted into the patient's body through small incisions. The surgical procedure is typically carried out by a surgeon through the use of elongated instruments inserted through these cannulas.

One common example of an arthroscopic procedure is a hip capsule closure. The hip capsule is a ligament that connects the top of the leg to the pelvis. During hip arthroscopy, capsule closure is typically the last step in the procedure. Capsule closer can be challenging to a surgeon, however, due to the number of steps that may be required and the use of multiple instruments (such as suture passers and retrievers) which need to be inserted and removed from the hip capsule multiple times. Retrieval of suture, for example, is typically accomplished by grasping the suture with regular forceps or other graspers having a suture capturing aperture formed at the distal tip when the forceps jaws are closed. Some suture retrievers include simple loops which extend from the tip of an elongated tube and which can be closed upon a suture passed through the loop. However, these devices are typically relatively complex to operate, making it harder for the average surgeon to utilize, and increasing the likelihood of device failure. Additionally, "gun" style suture passers, which pass a stitch through a distal jaw opening by squeezing the handle, are often large and bulky. The mechanisms involved in these types of suture passers also make them difficult to manufacture with the correct distal curvature required for access to the hip capsule.

SUMMARY

Described herein is a suture passing device which combines the low profile and optimal angle geometry of a standard suture passer with the functionality of a suture grasper. The device has a curved, slotted shaft with a piercing end and an integral suture grasper, allowing the surgeon to pierce through a first tissue portion with the device and extend a looped portion of monofilament loaded within the shaft into the repair site. The shaft is then rotated so that the monofilament is allowed to fall out of the shaft through the slot. The surgeon then pierces a second tissue portion with the device and extends the suture grasper to capture the looped portion of monofilament. The monofilament is retrieved through the second tissue portion and a suture is passed through the looped portion of the monofilament. Finally, the monofilament is used to pull the suture through the tissue and the suture is tensioned to close the hip capsule.

Further examples of the suture passing device of this disclosure and methods of use thereof may include one or more of the following, in any suitable combination.

In examples, methods of tissue repair of this disclosure include introducing a suture passing device into a repair site. The device includes a hollow shaft having a proximal end, a distal end, and a slot extending through a surface of the shaft from the proximal end to the distal end. A flexible member having a looped portion is loaded within the shaft. The method also includes inserting the device through a first pierce point in a first tissue portion such that the distal end of the shaft extends from the first pierce point, and extending the flexible member from the distal end of the shaft such that the looped portion of the flexible member extends from the first pierce point. The method also includes translating the shaft such that the flexible member is allowed to fall through the slot at the distal end of the shaft into the repair site.

Further examples of the method include inserting the device through a second pierce point in a second tissue portion adjacent the first tissue portion. A grasping member is extended from the device to grasp the looped portion of the flexible member. The grasping member is then retracted towards the distal end of the shaft to secure the flexible member to the device. The device and the looped portion of the flexible member are then retracted through the second tissue portion. In further examples, the method includes passing a suture through the looped portion of the flexible member. The free ends of the flexible member are then used to pull the suture through the first tissue portion and the second tissue portion. The suture is then tensioned to close a gap between the first tissue portion and the second tissue portion.

In yet further examples, extending the grasping member from the device incudes actuating a member on a handle coupled to the proximal end of the shaft, the actuating member being operatively coupled to the grasping member. In examples, the method further includes tying ends of the suture to secure the suture to the first and second tissue portions. In examples, the flexible member is a monofilament. In examples, inserting the device through the pierce point in the first tissue portion includes inserting the device through the pierce point with a pointed tip at the distal end of the shaft. In examples, introducing the device into the repair site includes introducing the device through a cannula. In further examples, the cannula is one of a 7.0 mm or 8.5 mm arthroscopic cannula, and the repair site is a hip capsule.

Examples of the suture passing device of this disclosure include a handle having a proximal end, a distal end, and a first slot extending along a longitudinal axis therebetween. The device also includes a hollow shaft, a proximal end of the shaft coupled to the first slot at the distal end of the handle. The shaft includes a second slot extending along a length of the shaft in communication with an interior of the shaft and configured to release a flexible member from the interior of the shaft. The first slot is axially aligned with the second slot. The device also includes a grasping member disposed within the shaft and configured to move along a length of the shaft between a retracted and an extended position. The grasping member includes at least one arm projecting from a distal end of the shaft when in the extended position.

In further examples, the device includes an actuator on a surface of the handle, the actuator operatively coupled to the grasping member to move the grasping member between the retracted and extended positions. In examples, the distal end of the shaft includes a pointed tip for penetrating tissue and a beveled opening. In examples, the distal end of the shaft is curved relative to the longitudinal axis of the handle. In examples, the angle of the curve relative to the longitudinal axis is about 70 degrees. In further examples, the at least one arm of the grasping member is two arms, and at least one of the two arms terminates in a hooked portion. In examples, a length of the at least two arms is substantially the same. In yet further examples, the at least two arms are biased to spring apart when in the extended position. In further examples, the device is configured to pass through at least one of a 7.0 mm or 8.5 mm arthroscopic cannula.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Figure 1:
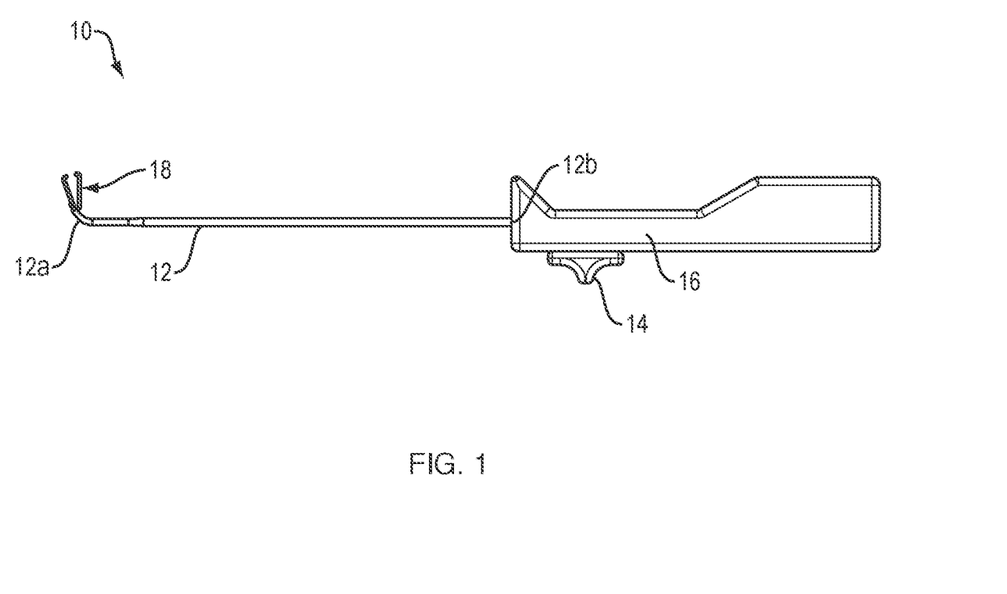
FIG. 1 is an example of a suture passing device of this disclosure in a side view.

Turning now to FIG. 1, a suture passing device 10 for manipulating and passing suture is shown in a side view. The device 10 generally comprises an elongated, hollow shaft 12 with a distal end 12a, and a handle 16 at a proximal end 12b of the shaft 12. An actuator 14 (for example, a lever, slide, or button) may be coupled to a surface of the handle 16. The actuator 14 is configured to control a grasping member 18 at the distal end 12a of the shaft 12, for example, by axial movement along a surface of the handle 16. The device 10 may be used to pass and/or retrieve suture through tissue, for example, during a capsule closure in a hip arthroscopy procedure. However, it is contemplated by this disclosure that the device 10 could be used in other types of arthroscopic procedures, such as a labrum or rotator cuff repair. In examples, the device 10 advantageously has a low profile which is configured to fit through a 7.0 mm or 8.5 mm arthroscopic cannula.

Figure 2A:
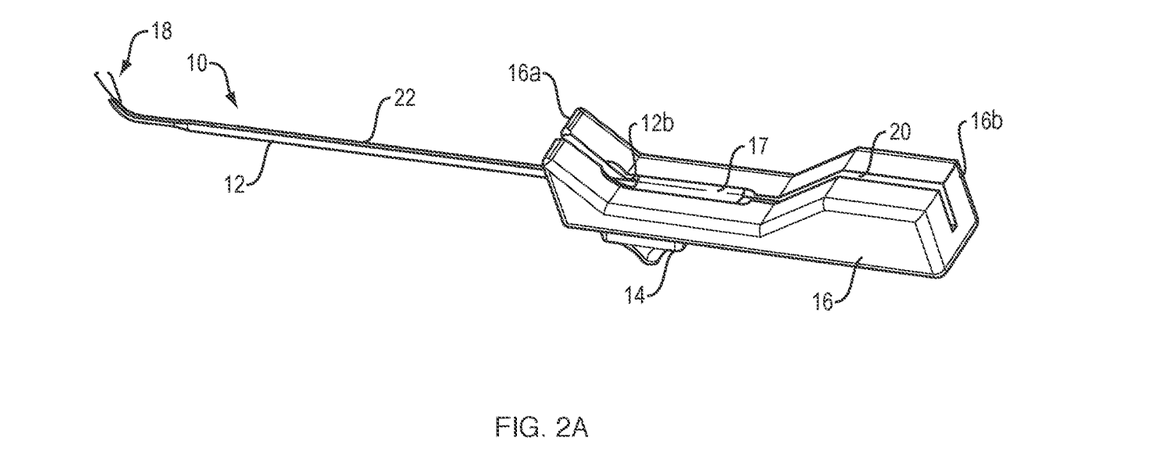
FIGS. 2A and 2B are perspective views of the suture passing device of FIG. 1.
Figure 2B:
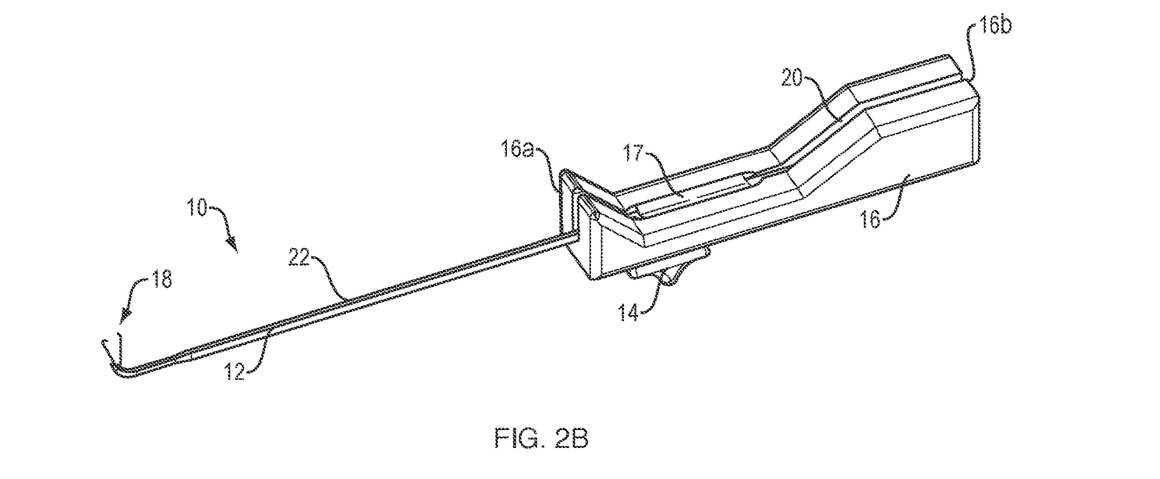

As shown in FIGS. 2A and 2B, the handle 16 includes a first longitudinal slot 20 extending from a distal end 16a to a proximal end 16b of the handle 16. The proximal end 12b of the shaft 12 extends into the slot 20 at the distal end 16a of the handle 16. As shown in FIGS. 2A and 2B, the slot 20 contains an area of wider diameter defining an actuator slot 17 in communication with the actuator 14. The shaft 12 further includes a second longitudinal slot 22 which is axially aligned with the first slot 20. The second slot 22 extends along a length of the shaft 12 in communication with an interior of the shaft 12. In examples, the various components of the device 10, including the shaft 12 and the handle 16, can be formed of one or more of a variety medical grade materials, including stainless steel, titanium, polycarbonate, Acrylonitrile butadiene styrene (ABS), polypropylene, acrylic, liquid crystal polymer (LCP), polyether-etherketone (PEEK), silicone, and thermoplastic elastomer (TPE).

Various different manufacturing techniques can be used to make and assemble the various components of the device 10. In examples, the various components of the device 10 are assembled via a press fit, overmolding, welding or other joining process.

Figure 3A:
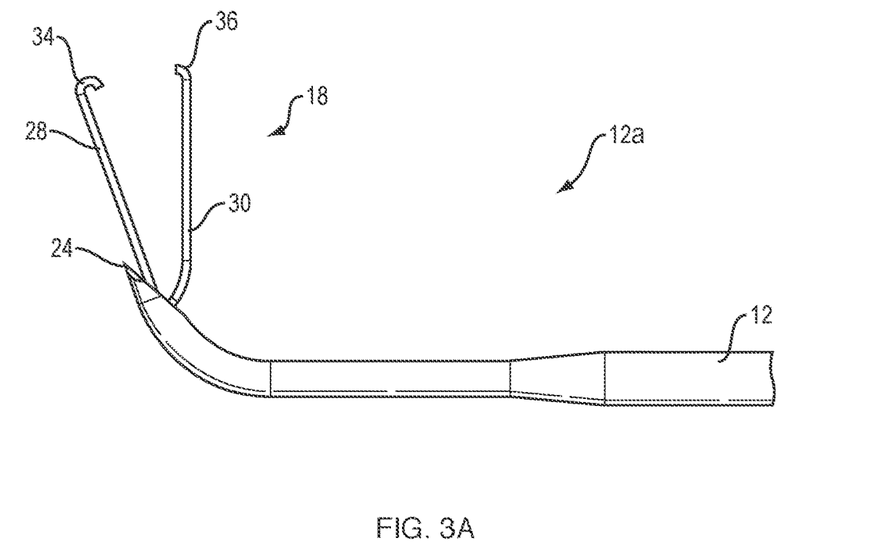
FIGS. 3A and 3B are detailed views of the distal end of the suture passing device of FIG. 1.
Figure 3B:
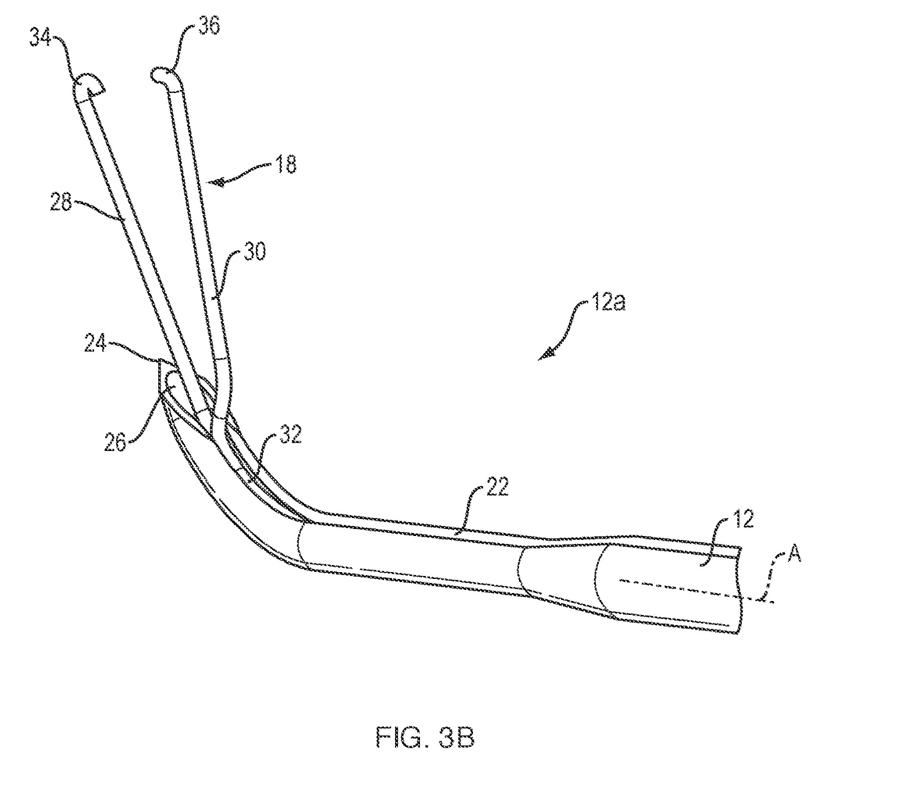

Detailed views of the distal end 12a of the shaft 12 are now illustrated in FIGS. 3A and 3B. In FIGS. 3A and 3B, the distal end 12a of the shaft 12 is shown having a pointed or tissue-penetrating distal tip 24. The distal tip 24 may be defined, for example, by a beveled opening 26. However, other tip geometries are contemplated by this disclosure. In examples, the distal end 12a of the shaft 12 may be curved or bent at an acute angle to provide an optimal angle geometry for accessing a repair site, such as a hip capsule. In examples, the angle of the bend relative to a long axis A of the shaft 12 is about 70 degrees. However, angles greater or less than 70 degrees are contemplated by this disclosure. Additional bend configurations, such as left/right helical bends, crescents, or other suitable geometries are also contemplated by this disclosure.

Still referring to FIGS. 3A and 3B, the grasping member 18 includes a pair of retractable, deformable wire arms 28, 30 projecting from the distal end 12a of the shaft 12 when in an extended position. While the grasping member 18 is shown in FIGS. 3A and 3B as comprising two arms 28, 30, it will be appreciated that more or fewer than two arms could be used. Both of the arms 28, 30 may be formed of stainless steel wire, Nitinol, or other suitable materials. The arms 28, 30 may be made of the same material or of a different material having a different tensile strength and/or degree of flexibility. In the extended position, the arms 28, 30 are biased to spring apart, but when they are retracted into the shaft 12, they are forced together.

Since closure of the arms 28, 30 requires a counterforce as the arms 28, 30 are retracted into the shaft 12, the counterforce may be provided by any number of internal geometries within the shaft 12. Examples of internal geometries may include a transverse bridge (not shown) which the arms 28, 30 pass under, such that when the arms 28, 30 are retracted, the bridge retains the arms 28, 30 against the inner diameter of the shaft 12. In other examples, the arms 28, 30 could be retracted inside of an adjacent, fully circumferential lumen (not shown) that ensures the closure of the arms 28, 30 when retracted. Thus, an axial motion of the arms 28, 30 creates an opening/closing motion of the arms 28, 30, which can be used for suture grasping and manipulation.

Still referring to FIGS. 3A and 3B, a length of one of the arms 28, 30 may be the same as, longer, or shorter than the length of the other arm 28, 30, although preferably the length of both of the arms 28, 30 is the same to prevent suture from being captured by one arm 28, 30 only. In examples, at least one of the arms 24, 26 (preferably the stronger/more rigid arm where present) terminates in a full hook 34 to aid in grasping suture. The other of the arms 28, 30 may terminate in a partial hook 36, as shown. In examples, the partial hook 36 may act as an arm to push the suture towards the arm with the full hook 34 and capture the suture during closure of the hooks 34, 36. However, it is contemplated by this disclosure that the other of the arms 28, 30 may terminate in another full hook or may be straight-sided. As shown in FIGS. 3A and 3B, when the arms 28, 30 are in the extended position, they are linearly aligned between the tip 24 and the slot 22 such that the hooks 34, 36 are curved in toward each other. It is further contemplated by this disclosure that a multiple hook configuration extending in a conical or other suitable geometric fashion aids in suture capturing.

In examples, each of the arms 28, 30 terminates in a linking member 32. The linking member 32 may be curved to accommodate the curvature at the distal end 12a of the shaft 12. The linking member 32 is operatively coupled, directly or indirectly, to the actuator 14 (FIG. 1) to move the arms 28, 30 between the extended and retracted positions, or to selected positions therebetween. In examples, the grasping member 18 is manufactured via wire drawing and bending, or through a metal stamping process as one component (e.g., in cases where the arms 28, 30 and the linking member 32 are stamped from a single piece of metal), which can reduce the likelihood of an arm 28, 30 breaking off from the grasping member 18 and thereby falling into the surgical cavity of the patient. However, other manufacturing techniques, such as die casting and injection molding, can alternatively or additionally be used.

Figure 4A:
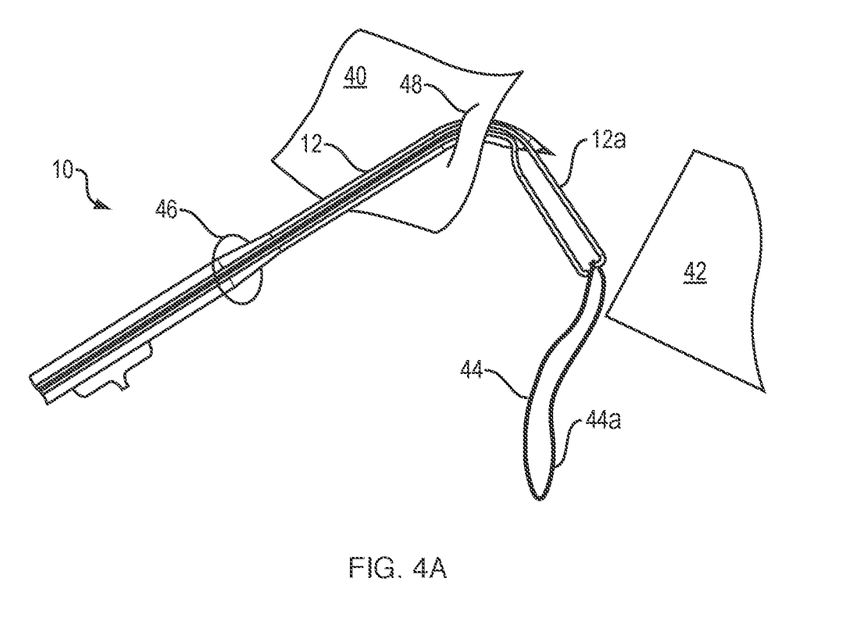
FIGS. 4A-E illustrate an example of a method of using the suture passing device of FIG. 1 in a hip capsule closure.
Figure 4B:
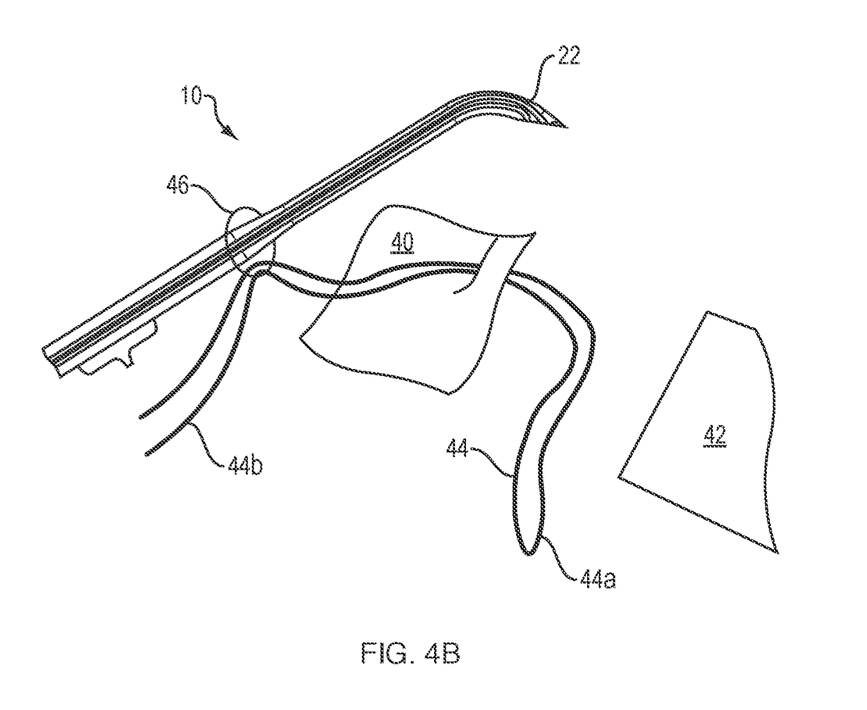

FIGS. 4A-E illustrate an example of a method of using the device 10 to close a gap between two pieces of tissue, for example, a first tissue portion 40 and a second tissue portion 42 of a hip capsule. To begin the procedure, the device 10 is first loaded with a looped portion 44a of a monofilament or other flexible member 44. As shown in FIG. 4A, the device 10 is passed through a portal 46 into the repair site and then through a first tissue portion 40 at a first pierce point 48. The monofilament 44 is then shuttled from the distal end 12a of the shaft 12, for example, by axial movement of the user's thumb along the actuator slot 17 in the handle 16, such that the looped portion 44a of flexible member 44 extends from the first pierce point 48. As shown in FIG. 4B, without removing the device 10 from the portal 46, the device 10 is retracted from the first tissue portion 40 and then rotated or otherwise translated to release the flexible member 44 from the device 10 through the slot 22. Consequently, the looped portion 44a of the flexible member 44 remains in the repair site while a second end 44b of the flexible member 44 is outside of the portal 46 and accessible to the user.

Figure 4C:
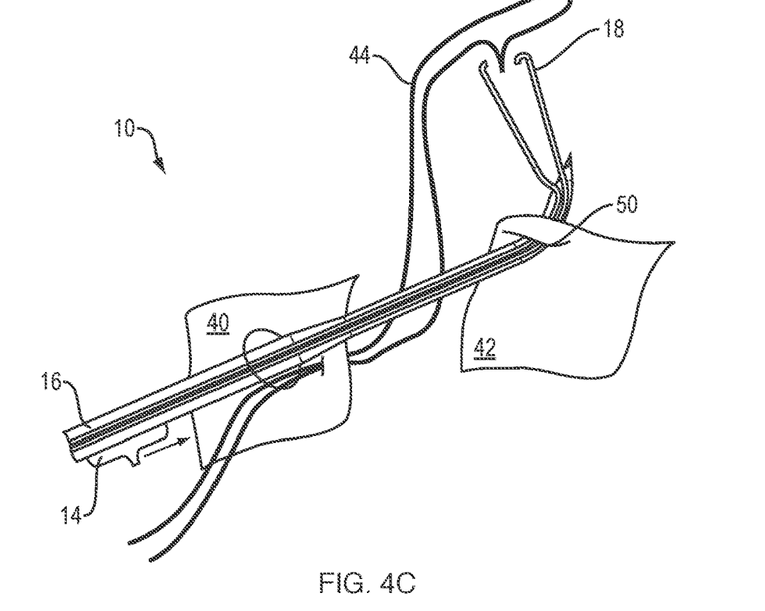
Figure 4D:
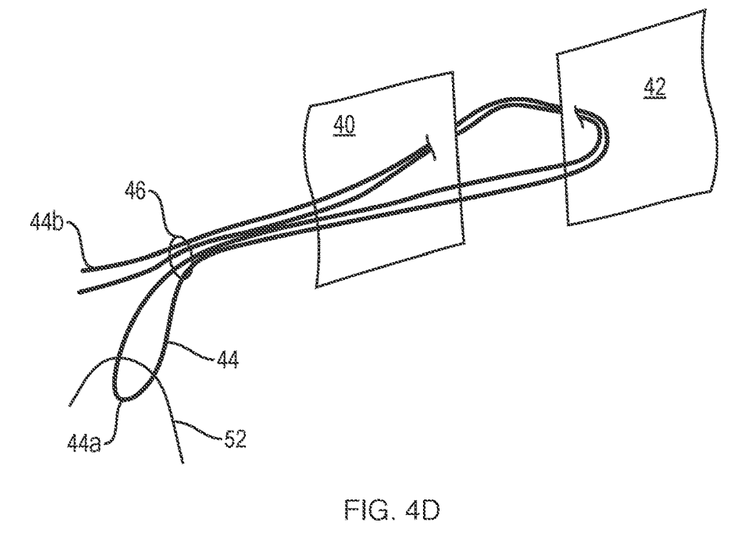
Figure 4E:
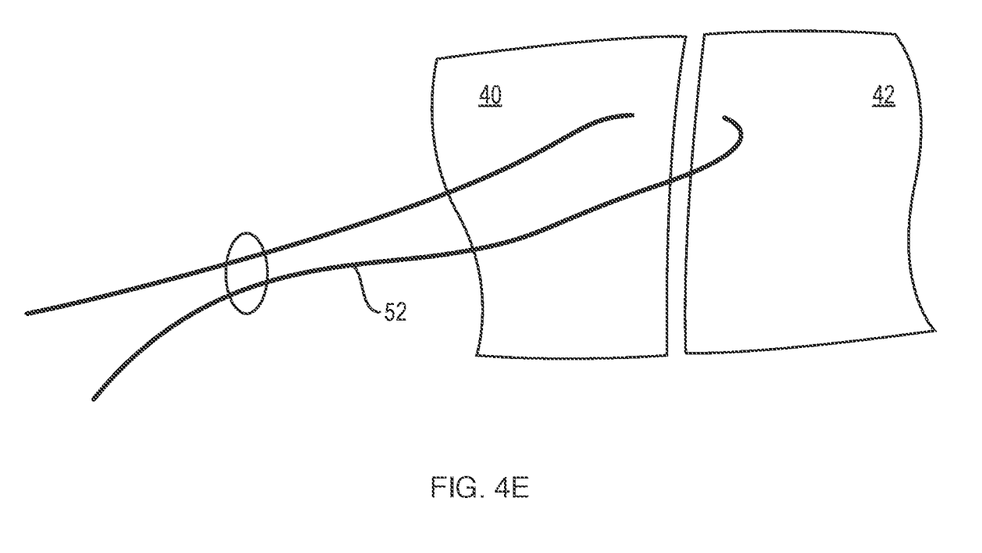

Turning now to FIG. 4C, the device 10 is pierced through the second tissue portion 42 at a second pierce point 50. The grasping member 18 is extended from the distal end 12a of the shaft 12 and the flexible member 44 is retrieved by the grasping member 18 through the second pierce point 50 of the second tissue portion 42. As shown in FIG. 4D, the device 10 is then withdrawn from the portal 46, simultaneously retrieving the looped portion 44a of the flexible member 44 through the portal 46. A strand of suture 52 is then passed through the looped portion 44a of the flexible member 44. The second end 44b of the flexible member 44 is then pulled to pass the suture 52 into the portal 46 and through the tissue portions 40, 42 to close the space between the tissue portions 40, 42 (FIG. 4E). The surgeon can then tie a knot in the suture 52 to close this portion of the hip capsule.

While the disclosure has been particularly shown and described with references to preferred examples thereof, it will be understood by those skilled in the art that various changes in form and details may be made therein without departing from the spirit and scope of the present application as defined by the appended claims. Such variations are intended to be covered by the scope of this present application. As such, the foregoing description of examples of the present application is not intended to be limiting, the full scope rather being conveyed by the appended claims.

The invention claimed is:

1. A method of tissue repair comprising:
   introducing a suture passing device into a repair site, the device comprising a hollow shaft having a proximal end, a distal end, and a slot extending through a surface of the shaft from the proximal end to the distal end, a flexible member having a looped portion being loaded within the shaft;
   inserting the device through a first pierce point in a first tissue portion such that the distal end of the shaft extends from the first pierce point;
   extending the flexible member from the distal end of the shaft such that the looped portion of the flexible member extends from the first pierce point; and
   translating the shaft such that the flexible member is allowed to fall through the slot at the distal end of the shaft into the repair site.

2. The method of claim 1, further comprising:
   inserting the device through a second pierce point in a second tissue portion adjacent the first tissue portion;
   extending a grasping member from the device to grasp the looped portion of the flexible member;
   retracting the grasping member towards the distal end of the shaft to secure the flexible member to the device; and
   retracting the device and the looped portion of the flexible member through the second tissue portion.

3. The method of claim 2, further comprising:
   passing a suture through the looped portion of the flexible member;
   using free ends of the flexible member, pulling the suture through the first tissue portion and the second tissue portion; and
   tensioning the suture to close a gap between the first tissue portion and the second tissue portion.

4. The method of claim 2, wherein extending the grasping member from the device comprises actuating a member on a handle coupled to the proximal end of the shaft, the actuating member being operatively coupled to the grasping member.

5. The method of claim 2, further comprising tying ends of the suture to secure the suture to the first and second tissue portions.

6. The method of claim 1, wherein the flexible member is a monofilament.

7. The method of claim 1, wherein inserting the device through the pierce point in the first tissue portion comprises inserting the device through the pierce point with a pointed tip at the distal end of the shaft.

8. The method of claim 1, wherein introducing the device into the repair site comprises introducing the device through a cannula.

9. The method of claim 8, wherein the cannula is one of a 7.0 mm or 8.5 mm arthroscopic cannula.

10. The method of claim 1, wherein the repair site is a hip capsule.

11. A suture passing device comprising:
- a handle having a proximal end, a distal end, and a first slot extending along a longitudinal axis therebetween;
- a hollow shaft, a proximal end of the shaft coupled to the first slot at the distal end of the handle, the shaft comprising a second slot extending along a length of the shaft in communication with an interior of the shaft and configured to release a flexible member from the interior of the shaft, the first slot being axially aligned with the second slot; and
- a grasping member disposed within the shaft and configured to move along a length of the shaft between a retracted and an extended position, the grasping member including at least one arm projecting from a distal end of the shaft when in the extended position.

12. The device of claim 11, further comprising an actuator on a surface of the handle, the actuator operatively coupled to the grasping member to move the grasping member between the retracted and extended positions.

13. The device of claim 11, wherein the distal end of the shaft comprises a pointed tip for penetrating tissue.

14. The device of claim 11, wherein the distal end of the shaft comprises a beveled opening.

15. The device of claim 11, wherein the distal end of the shaft is curved relative to the longitudinal axis of the handle.

16. The device of claim 15, wherein the angle of the curve relative to the longitudinal axis is about 70 degrees.

17. The device of claim 11, wherein the at least one arm of the grasping member is two arms, and wherein at least one of the two arms terminates in a hooked portion.

18. The device of claim 17, wherein a length of the at least two arms is substantially the same.

19. The device of claim 17, wherein the at least two arms are biased to spring apart when in the extended position.

20. The device of claim 11, wherein the device is configured to pass through at least one of a 7.0 mm or 8.5 mm arthroscopic cannula.

* * * * *